US007632644B2

(12) United States Patent
Weichert et al.

(10) Patent No.: US 7,632,644 B2
(45) Date of Patent: Dec. 15, 2009

(54) IMAGING AND SELECTIVE RETENTION OF PHOSPHOLIPID ETHER ANALOGS

(75) Inventors: Jamey P. Weichert, Fitchburg, WI (US); Marc Longino, Verona, WI (US); Sharon Weber, Madison, WI (US); Joseph O. Nwankwo, Madison, WI (US)

(73) Assignee: Cellectar, Inc., Madison, WI (US)

( * ) Notice: Subject to any disclaimer, the term of this patent is extended or adjusted under 35 U.S.C. 154(b) by 486 days.

(21) Appl. No.: 11/382,645

(22) Filed: May 10, 2006

(65) Prior Publication Data

US 2006/0228298 A1    Oct. 12, 2006

Related U.S. Application Data

(63) Continuation-in-part of application No. 11/177,749, filed on Jul. 8, 2005, and a continuation-in-part of application No. 11/316,620, filed on Dec. 20, 2005, and a continuation-in-part of application No. 10/906,687, filed on Mar. 2, 2005, and a continuation-in-part of application No. PCT/US2005/024259, filed on Jul. 8, 2005, and a continuation-in-part of application No. PCT/US2005/047657, filed on Dec. 20, 2005, and a continuation-in-part of application No. PCT/US2005/006681, filed on Mar. 2, 2005.

(60) Provisional application No. 60/594,832, filed on May 10, 2005, provisional application No. 60/521,831, filed on Jul. 8, 2004, provisional application No. 60/593,190, filed on Dec. 20, 2004, provisional application No. 60/521,166, filed on Mar. 2, 2004.

(51) Int. Cl.
*C12Q 1/68*      (2006.01)
*C12P 19/34*     (2006.01)
*G01N 33/53*     (2006.01)

(52) U.S. Cl. ............................ 435/6; 435/7.1; 435/91.2

(58) Field of Classification Search ........................ None
See application file for complete search history.

(56) References Cited

U.S. PATENT DOCUMENTS

| 4,925,649 | A | 5/1990 | Counsell et al. |
| 4,965,391 | A | 10/1990 | Counsell et al. |
| 5,087,721 | A | 2/1992 | Counsell et al. |
| 5,347,030 | A | 9/1994 | Counsell et al. |
| 5,369,097 | A | 11/1994 | Salari et al. |
| 5,795,561 | A | 8/1998 | Counsell et al. |
| 6,417,384 | B1 | 7/2002 | Counsell et al. |
| 2002/0065429 | A1 | 5/2002 | Counsell et al. |

OTHER PUBLICATIONS

Arthur, G. et al., The Inhibition of Cell Signaling Pathways . . . R. Biochim Biophys Acta. (1998) 1390:85-102.
Becher, R. et al., Phase II Trial of Orally Administered Miltefosine . . . Onkologie-Germany (1993) 16; 1:11-15.
Berdel, W.E. et al., Daily Oral Miltefosine (Hexadecylphosphocholine) . . . Onkologie-Germany (1992) 15:238-242.
Clezy, P.S. et al., The Chemistry of Pyrrolic Compounds, Aust. J.Chem., (1969) 22:239-49.
Counsell, R.E. et al., Tumor Visualization With a Radioiodinated Phospholipid . . . (1990) 31; 3:332-336.
Counsell, R.E. et al, Synthesis and Evluation of Radioiodinated Phospholipd Ether . . . Quart J. Nucl Med. (1997) 41(suppl 1):14.
Curley, SA et al., Radiofrequency Ablation of Unresectable Primary and Metastitic . . . Ann Surg. (1999) 230:1-8.
De Gramont, A. et al., Randomized Trial Comparing Monthly Low-Dose Leucovorin and . . . J. Clin. Oncol. (1997) 15:808-815.
Fong,Y. et al., Clinical Score for Predicting Recurrence After Hepatic Resection . . . Ann Surg. (1999) 230:309-321.
Giacchetti, S. et al., Phase III Multicenter Randomized Trial of Oxaliplatin Added . . . J. Clin. Oncol. (2000) 18:136-147.
Greven, K. et al., Can Positron Emission Tomography Distinguish Tumor . . . Cancer Journal Scientifica American (1997) 3:353-357.
Ike, H. et al., Results of Agressive Resection of Lung Matastases From Colorectal Carcinoma . . . Dis colon Rectum (2002) 45:468-473.
Imboden, M. et al., The Level of MHC Class I Expression on Murine Adenocarcinoma Can Change . . . Cancer Res. (2001) 61:1500-1507.
Kallman, R. F. Rodent Tumor Models in Experimental Cancer Therapy Pergamon Press, New York, (1987) pp. 111-132.
Lencioni, R. et al., Percutaneous Radiofrequency Thermal Ablation of Liver Malignancies: Techniques . . . Abdom Imaging (2001) 26:345-360.
Liebeskind L.S. et al., Heteroaromatic Thioether—Bornic Acid Cross-Coupling . . . Dept. of Chem., Emory University, Organic Letters (2002) 4; 6:979-981.
Longino, M.A. et al., Tumor Selective Rentention of NM404—Involvement of Phospholipase D. Molecular Imaging (2004), 3(3), 257.
Maier, O. et al., Fluorescent Lipid Probes: Some Properties and Application (A Review) Chemistry and Physics of Lipids 116 (2002) 3-18.
Mayr, N. A. et al., Method and Timing of Tumor Volume Measurement for Outcome . . . Int. J. of Rad., Oncol., Bio., Phys. (2002) 52; 1:14-22.
Meta-Analysis:Modulation of Fluorouracil by . . . Advanced Colorectal Cancer Meta-Analysis Project. J. clin. Oncol. (1992) 10:896-903.
Moser, A.R. et al., Specificity of NM404 for Hyperplasia Versus Neoplasia in the . . . Online Aug. 15-18, 2003 Presentation No. 305.
O'Dwyer, P.J. et al., Follow-Up of Stage B and C Colorectal Cancer in the United States and . . . Seminars in Onology (2001) 28:Suppl-9, 45-49.
Penna, C., et al., Colorectal Metastasis (Liver and Lung), Surg. clin. North Amer. (2002) 82:1075-1090.
Pickhardt, P.J. et al., Computed Tomographic Virtual Colonoscopy to Screen for Colorectal . . . NE J. Med. (2003) 349; 23:2191-2200.

(Continued)

*Primary Examiner*—James Martinelli
(74) *Attorney, Agent, or Firm*—Wood, Phillips, Katz, Clark & Moritmer

(57) ABSTRACT

The present invention generally relates to imaging and selective retention of phospholipid ether analogs in various neoplastic tissues. Specifically, the present invention relates to imaging and methods for selective retention of analogs, for example, NM404, in cancers such as Colorectal Cancer.

9 Claims, 5 Drawing Sheets

OTHER PUBLICATIONS

Plotzke, K.P. et. al., Selective Localization of a Radioiodinated Phospholipid Ether Analog in Human Tumor . . . J. Nucl. Med. (1993) 34(5):787-792.

Plotzke, K.P. et al., Selective Localization of Radioiodinated Alkylphosphocholine . . . Int. J. RadPart B, Nucl. Med. & Biology, (1992) 19(7):765-773.

Rampy, M.A. et al., Biological Disposition and Imaging of a Radioiodinated Alkylphosphocholine in Two Rodent . . . J. Nucl. Med. (1996) 37(9):1540-1545.

Rampy, M.A. et al., Synthesis and Biological Evaluation of Radioiodinated Phospholipid Ether Stereoisomers, J. Med. Chem. (1995) 38:3156-3162.

Saltz, L.B. et al., Irinotecan Plus Fluorouracil and Leucovorin for Metastiatic Colorectal Cancer . . . , N. Engl. J. Med. (2000) 343:905-91.

Snyder, F. et al., Alkyl and Alk-1-Enyl Ethers of Glycerol in Lipids From Normal and Neoplastic Human Tissues, Cancer Research. (1969) 29:251-257.

Snyder, F. et al., Occurrence and Nature of O-Alkyl and O-Alkyl-L-Enyl Moieties of Glycerol in Lipids of Morris . . . Biochem Biophys Acta. (1969) 176:502-510.

Solbiati, L. et al., Percutaneous Radio-Frequency Ablation of Hepatic Metastases From Colorectal Cancer: Long-Term . . . Radiology (2001) 221:159-166.

Stahl, A. et al., PET/CT Molecular Imaging in Abdominal Oncology, Abdominal Imaging (2004) 29:3(388-397).

Terwogt, J.M.M. et al., Phase II Trial of Topically Applied Miltefosine Solution in Optients With Skin-Metastasized . . . British J. of Cancer (1999) 79:1158-1161.

Wagner, R. et al., Boron-Dipyrromethene Dyes for Incorporation in Synthetic Multi-Pigment Light-Harvesting Arrays, Pure & Appl. Chem., (1996) 68; 7:1373-1380.

Weber, S.M. et al., Interleukin-1 Gene Transfer Results in CD8-Dependent Regression of Murine CT26 Liver Tumors, Ann. Surg. Oncol. (1999) 6:186-194.

Weichert, J.P. et al., Initial Clinical Imagining Results With NM404 in Non-Small Cell Lung Cancer, Molecular Imaging Online (2004) 3; 3:269-270.

Wichmann, M.W. et al., The Colorectal Cancer Study Group. Carcinoembryonic Antigen for the Detection . . . Anticancer Research (2000) 20:4953-4955.

Zasadny, K.R. et al., Predicted Dosimetry for I-131-NM404, A Phospholipid Ether Agent for Tumor Imaging and Possible Therapy, J Nucl Med. (1999) 40(5):39P.

Sik, M.D. et al., Neoplastic Transformation and Tumorrigensis Associated With Overexpress . . . Database Biosis(Online) (Oct. 2001) XP002365147 Database No. PREV200100523916.

Hirokazu O. et al., Increased Activity and Expression of Phospholipase D2 in Human . . . Database Biosis (Online) (2003) XP002365146 Database No. PREV00300566956.

Dong-Young, N. et al., Overexpression of Phospholipase D1 in Human Breast Cancer Tissues, Database Biosis (Online) (Dec. 2000) XP002365186 Database No. PREV200100047408, Abstract Only.

Weichert, J. et al., Specificity of NM404 for Hyperplasia versus Neoplasia in the APC . . . Oasis—Online Abstrct Submission and Invitation System, 1996-2007.

Weichert JP et al "Evaluation of 125I-NM404 in a Spontaneous Murine Pancreatic Adenocarcinoma . . . ", Aug. 2003, 2nd Annual Meeting of the Society of Molecular Imaging.

Weichert J. et al., Radioiodination Via Isotope Exchange in Pivalic Acid, Appl. Radiat Isot (1986) vol. 37, No. 8, 907-913.

Weichert J. et al., Polyiodinated Triglyceride Analogs as Potential Computed Tomography Imaging Agents for the Liver, J Med Chem (1995) 38, 636-646.

Pinchuk A. et al., Synthesis and Structure-Activity Relationship Effects on the Tumor Avidity of Radioiodinated Phospholipid Ether Analogues, J Med Chem (2006), 49, 2155-2165.

IMAGING AND SELECTIVE RETENTION OF PHOSPHOLIPID ETHER ANALOGS

RELATED APPLICATIONS

The present application seeks priority from U.S. Provisional Application No. 60/594,832 filed on May 10, 2005 and is a Continuation-In-Part of U.S. Non-Provisional application Ser. No. 11/177,749 and PCT/US05/24259 both of which were filed on Jul. 8, 2005, and both of which seek priority from U.S. Provisional Application 60/521,831 filed on Jul. 8, 2004. This application is a Continuation-In-Part of U.S. Non-Provisional application Ser. No. 11/316,620 and PCT/US05/47657, both of which were filed on Dec. 20, 2005, and both of which seek priority from U.S. Provisional application 60/593,190 filed on Dec. 20, 2004. This application is a Continuation-In-Part of U.S. Non-Provisional patent application Ser. No. 10/906,687 and PCT/US05/06681 both of which were filed on Mar. 2, 2005, and both of which seek priority from the U.S. Provisional Application No. 60/521,166 filed on Mar. 2, 2004. All these applications are incorporated by reference in their entirety, as if fully set forth herein.

TECHNICAL FIELD

The present invention generally relates to imaging and selective retention of phospholipid ether analogs. Specifically, the present invention relates to imaging and methods for selective retention of phospholipid ether analogs, such as NM404 in cancers, such as Colorectal Cancer.

BACKGROUND

Imaging various types of cancers is clinically important since early diagnosis most directly correlates with prognosis of a patient. For example, approximately 130,000 new cases of colorectal cancer are diagnosed each year in the United States. Thus colorectal cancer is the fourth most common cancer in the U.S., accounting for 60,000 deaths per year. Treatment depends primarily on the cancer stage, but may include surgery, radiation, and/or chemotherapy. Although the majority of patients can be treated with curative surgical resection of the primary tumor, between 10-75% of the patients recur, depending on the stage. At the time of recurrence, the most common site of metastases is the liver, followed by the lung. In patients with metastatic disease, surgery is the only potentially curative option and has become widely accepted for patients with isolated liver or lung metastases. However, even if resection is possible, the five-year survival is between 25-50% after complete resection of liver or lung metastases. Unfortunately, the majority of patients with metastatic disease are not candidates for surgery because of advanced disease. Although the median survival for patients with metastatic colorectal cancer has improved with modern chemotherapeutic regimens, these patients are not curable. Thus there is a need for earlier detection of metastatic disease by improving imaging modalities for staging patients with colorectal cancer.

Imaging plays an essential role both in staging patients at the time of diagnosis and evaluating for recurrence during follow-up. The standard imaging test to evaluate for metastases is a contrast-enhanced abdominal and pelvic CT scan. However, even with good quality dynamic CT, recurrences are rarely detected early enough to be amenable to curative resection. Clearly, in order for patients with metastatic disease to be candidates for curative resection, detecting the disease at an early stage is vital. Accordingly, there is a need for development of additional methods for detection of metastatic or recurrent diseases.

SUMMARY OF THE INVENTION

The present invention generally relates to imaging and selective retention of phospholipid ether analogs in various neoplastic tissues. Specifically, the present invention relates to imaging and methods for selective retention of analogs, for example, NM404, in cancers such as Colorectal Cancer. In one exemplary embodiment, the present invention provides a method of detecting neoplasia in a tissue sample from a patient having a phospholipase D (PLD) comprising the step of: (1) quantifying the PLD protein activity level or the PLD mRNA level in the tissue sample; and (2) determining whether the tissue sample has a lower level of protein activity than control or surrounding tissue region(s) wherein a lower activity region indicates detection and location of the neoplasia, or (3) determining whether the tissue sample has a lower level of mRNA than control or surrounding tissue region(s) wherein a lower mRNA level region indicates detection and location of the neoplasia. In this method the PLD protein activity or the mRNA level is quantified by quantitative PCR (QPCR).

Further, once the presence of the neoplastic tissue is determined then in this method, the patient having the lowered PLD protein activity level or the PLD mRNA is further administered with a PLE analog. This PLE analog is preferably selected from:

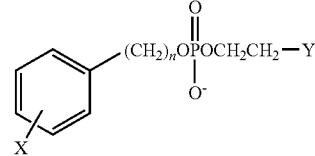

where X is selected from the group consisting of radioactive isotopes of halogen; n is an integer between 8 and 30; and Y is selected from the group comprising $NH_2$, $N(R)_2$, and $N(R)_3$, wherein R is an alkyl or arylalkyl substituent or

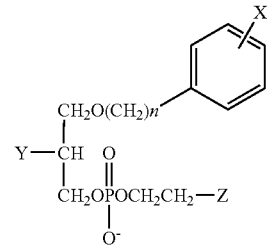

where X is a radioactive isotope of halogen; n is an integer between 8 and 30; Y is selected from the group consisting of H, OH, COOH, COOR and OR, and Z is selected from the group consisting of $NH_2$, $N(R)_2$, and $N(R)_3$, wherein R is an alkyl or arylalkyl substituent. In this method the administration of the PLE analog in the patient results in the treatment or reduction of said neoplasia in the patient.

As for the PLE compound used in this method, preferably, in the compound X is selected from the group of radioactive halogen isotopes consisting of $^{18}F$, $^{36}Cl$, $^{76}Br$, $^{77}Br$, $^{82}Br$, $^{122}I$, $^{123}I$, $^{124}I$, $^{125}I$, $^{131}I$ and $^{211}At$. More preferably, the phospholipid ether is 18-(p-Iodophenyl)octadecyl phosphocholine, 1-O-[18-(p-Iodophenyl)octadecyl]-1,3-propanediol-3-phosphocholine, or 1-O-[18-(p-Iodophenyl)octadecyl]-2-O-methyl-rac-glycero-3-phosphocholine, wherein iodine is in the form of a radioactive isotope.

Also in this method, the tissue having the PLD is isolated with laser capture microdissection prior to quantifying the PLD protein level activity or the PLD mRNA activity using QPCR. This method is useful in selectively removing neoplstic tissue from the surrounding tissue. Once the neoplastic tissue is separated, PLD levels are measured in this tissue and compared to the surrounding tissue or the control. Typically, the average ratio of PLD mRNA level in the control or the normal surrounding tissue to the neoplastic tissue is expected to about 1.1 to about 3000. Higher ratio makes the patient a better candidate for receiing therapy treatment using NM404 compound or other PLE analogs as described in this invention. Once the PLE analog is administered to the patient, it is further detected by PET, CT, MRI scanning methods and combination thereof. In a preferred embodiment, the neoplasia is selected from the group consisting of Lung cancer, Adrenal cancer, Melanoma, Colon cancer, Colorectal cancer, Ovarian cancer, Prostate cancer, Liver cancer, Subcutaneous cancer, Squamous cell cancer, Intestinal cancer, Hepatocellular carcinoma, Retinoblastoma, Cervical cancer, Glioma, Breast cancer, Pancreatic cancer and Carcinosarcoma.

In another exemplary embodiment, the present invention teaches methods for screening anti-tumor compounds using the PLD activity levels. In this methodology the fluorescent, luminescent or radiolabeled anti-tumor agent is selected by a method of screening a tissue sample from a patient having a PLD. The screening steps include the following: (i) contacting the anti-tumor agent with the tissue sample; (ii) detecting the selective retention of the anti-tumor agent in the tissue sample; (iii) quantifying the PLD protein activity or PLD mRNA level in the tissue sample, wherein reduced PLD protein activity or reduced mRNA level compared to control or surrounding tissue region(s) is indicative of a neoplasitic tissue; and (iv) determining whether the neoplastic tissue sample of step (iii) selectively retains the anti-tumor agent by comparing the anti-tumor agent retention in the control or the surrounding tissue region(s) to the retention in the neoplastic tissue sample wherein a lower retention in the control or the surrounding tissue as compared to the neoplastic tissue sample is indicative of tumor-selective anti-tumor compound.

Inventors believe that using this screening method which employs the mechanistic retention of PLE analogs in neoplastic tissues, other anti-tumor agents which have similar mechanistic pathway may also be discovered where lowered PLD levels allows for selective retention of these anti-tumor agents. In this method, the anti-tumor agent is detected by PET imaging, CT imaging, MRI imaging, fluorescence imaging, or combinations thereof. Hoever, other methodology known to one of ordinary skill in the art may also be used.

In yet another exemplary embodiment, the present invention provides a method of identifying a patient having neoplasia for receiving treatment with phospholipid analog of claim 3, comprising the steps of: (i) removing a tissue sample from a patient having a phospholipase D (PLD); (ii) quantifying the PLD protein activity level or the PLD mRNA level in the tissue sample, wherein a lower level of protein activity level or PLD mRNA level than control or surrounding tissue region(s) indicates detection and location of the neoplasia; and (iii) administering to the patient having a PLD mRNA ratio of about 1.1 to about 3000 in the control or the normal surrounding tissue to the neoplastic tissue with a PLE analog as described above. Inventors believe that this method can be used as an important screening method for determining and identifying which patients having neoplasia would be good candidates for receiving the PLE analog treatment.

Further objects, features and advantages of the invention will be apparent from the following detailed description, drawings and appended claims.

DETAILED DESCRIPTION OF THE PREFERRED EMBODIMENTS

A: General

Figure 1:
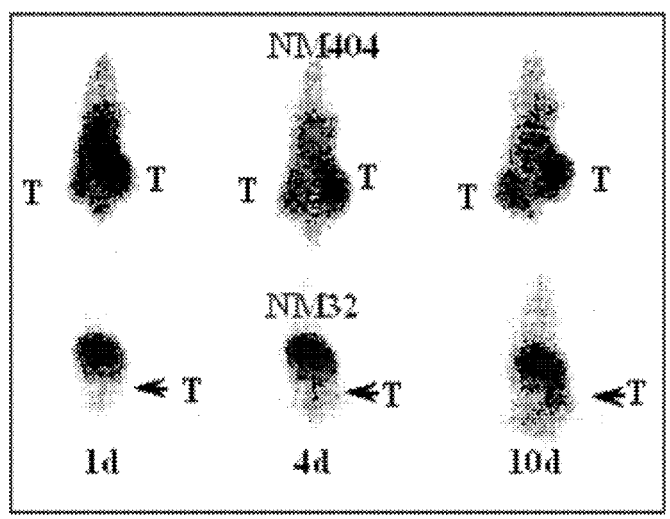
FIG. 1 depicts SPECT images, comparing NM404 and NM324 in SCID mouse tumor model. Note that most of the NM324 activity is found in the gut and not in the tumor (implanted in the thigh) whereas NM404 identified one tumor in both the left and right thigh (T=Tumor).

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As defined herein, "contacting" means that the anti-tumor compound used in the present invention is introduced into a sample containing the receptor in a test tube, flask, tissue culture, chip, array, plate, microplate, capillary, or the like, and incubated at a temperature and time sufficient to permit binding of the anti-tumor compound to a receptor. Methods for contacting the samples with the anti-tumor compound or other specific binding components are known to those skilled in the art and may be selected depending on the type of assay protocol to be run. Incubation methods are also standard and are known to those skilled in the art.

In another embodiment, the term "contacting" means that the anti-tumor compound used in the present invention is introduced into a patient receiving treatment, and the compound is allowed to come in contact in vivo.

As used herein, the term "treating" includes preventative as well as disorder remittent treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a patient, tissue, organ or cells in contact with an anti-tumor phospholipid ether compound. As used herein, administration can be accomplished in vitro, i.e. in a test tube, or in vivo, i.e. in cells or tissues of living organisms, for example, humans. In certain embodiments, the present invention encompasses administering the compounds useful in the present invention to a patient or subject. A "patient" or "subject", used equivalently herein, refers to a mammal, preferably a human, that either: (1) has a disorder remediable or treatable by administration of the anti-tumor substance using a phospholipid ether compound or (2) is susceptible to a disorder that is preventable by administering the anti-tumor compound using a phospholipid ether compound.

B. Preferred Embodiments

The present application provides a series of experiments evaluating phospholipid ether analogs (PLE), such as NM404, which can be radiolabeled for imaging and/or therapeutic applications. Various PLE analogs are described in U.S. Pat. Nos. 4,925,649; 4,965,391; 5,087,721; 5,347,030 and 6,417,384; all of which are herein incorporated by reference. Phospholipid ether analogs, such as NM404, are novel agents that are taken up and retained within tumor cells for a prolonged time in a variety of implanted animal tumors. Following experiments highlight the use of phospholipid ether analogs, such as radiolabeled NM404 to image implanted human colorectal tumors, and evaluate the mechanism of selective retention of NM404 in human colorectal cancer cell lines and tissues. Following experiments and examples are for illustrative purposes only. The invention accordingly should not be deemed to be limited to either colorectal cancer or NM404 phospholipid ether analog only.

NM404

NM404 is a phospholipid ether analog which can be labeled with any of the radioisotopic forms of halogen, such as iodine. Other radioisotopes that may be used include $^{18}F$, $^{36}Cl$, $^{76}Br$, $^{77}Br$, $^{82}Br$, $^{122}I$, $^{123}I$, $^{124}I$, $^{125}I$, $^{131}I$ and $^{211}At$. Because NM404 is retained in tumor cells for a prolonged time (in excess of 60d in some models) and because it can be bound to radioiodinated isotopes such as $^{125}I$, $^{131}I$, or $^{124}I$, it may serve as an ideal mechanism for prolonged delivery of radioisotope to tumor by means of a simple intravenous injection. These findings may result in important implications for tumor imaging, and even more significant, for tumor therapy.

Figure 2:
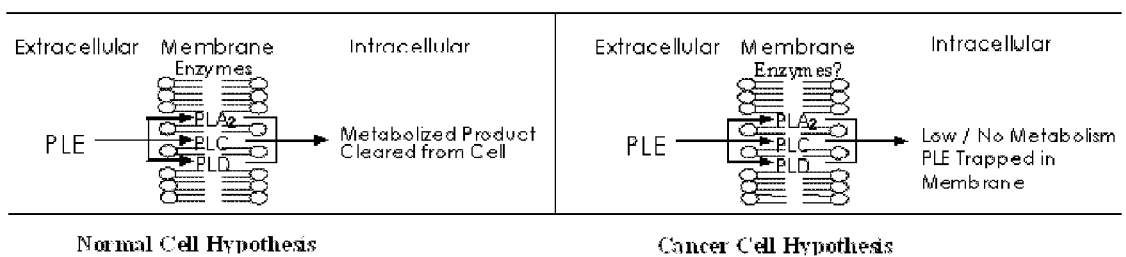
FIG. 2 depicts the prevailing hypothesis for the selective retention of phospholipid ether analogs (PLE).

Radioiodinated NM404, a second-generation phospholipid ether analog, has displayed remarkable tumor selectivity in multiple xenograft and spontaneous primary and metastatic rodent tumor models. The prevailing hypothesis of this approach is that phospholipid ether analogs become trapped exclusively in tumor cell membranes because of their inability to undergo metabolism and elimination, as seen in FIG. 2. Thus, the differential clearance rates of phospholipid ethers from normal cells versus viable tumor cells form the basis of this concept.

Tumor imaging with NM404 can be performed using either $^{131}I$ for gamma imaging with SPECT (2-dimensional, FIG. 1) or $^{124}I$ for imaging with PET (3-dimensional), which is much more accurate in anatomically localizing tumors. Thus, utilizing $^{124}I$ to label NM404 for imaging with PET is a novel application that may have a significant impact on the ability to accurately stage patients prior to surgical resection. This may affect the ability to detect tumors early in their course, stage primary tumors at the time of diagnosis, and follow patients after surgical resection of tumor in order to detect cancer recurrence early. In addition, and perhaps more importantly, radiolabeled NM404 may have crucial therapeutic applications using $^{131}I$-NM404 in a variety of tumor types.

Mechanism for Selective Retention

Figure 7:
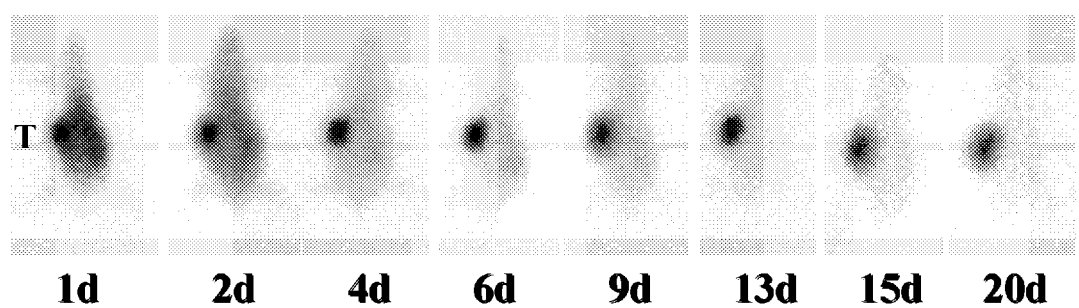
FIG. 7 depicts NM404-Human RL-251 Adrenal CA: Time Course for prolonged tumor retention for $^{125}$I-NM404 (10 µCi) in SCID mouse with human RL-251 adrenal tumor xenograft.

Preliminary data has revealed that the likely mechanism for the prolonged retention of NM404 in murine tumors is a defect in an isoform of phospholipase D (PLD), an enzyme found in the cell membrane that is likely responsible for the breakdown and clearance of NM404 in normal cells. See also FIG. 7, which depicts selective retention as of $^{125}I$-NM404 (10 µCi) SCID mouse with human RL-251 adrenal tumor xenograft after 20 days.

Therefore, if the radiolabeled NM404 successfully localizes in human colorectal cancer in a SCID mouse then the tissue distribution studies in these animals will reveal a high % injected dose/tumor ratio. In addition, if the mechanism for the selective retention of NM404 is because of a defect in $PLD_1$, then an isoform of PLD, which is manifested in tumor cells will display: (1) a decrease in $PLD_1$ mRNA, (2) a decrease in total $PLD_1$ protein, and (3) a decrease in $PLD_1$ protein activity.

In order to study the selective retention mechanism of the phospholipid ether compound, following measures may be taken: (a) Evaluate the uptake of radiolabeled NM404 in an implanted human colorectal cancer in SCID mice using microPET and tissue distribution assays; (b) Evaluate the mechanism of selective retention of NM404 in human colorectal cancer cell lines. (c) Evaluate the mechanism of selective retention of NM404 in human colorectal cancer tissue.

I. Evaluate the Uptake of Radiolabeled NM404 in an Implanted Human Colorectal Cancer in SCID Mice Using microPET and Tissue Distribution Assays In order to evaluate uptake of NM404 first, quantify uptake of $^{124}I$-NM404 and in LS-180 human colorectal cancer in SCID mice using micro PET images compared to necropsy specimens, and second, perform issue distribution studies using $^{125}I$-NM404 in a LS-180 human colorectal cancer model to quantitate uptake of NM404 and compare to quantification of microPET images.

Generally, implanted human colorectal cancers will exhibit high levels of selective retention of radioiodinated NM404 on microPET and on standard tissue distribution assays. NM404 can be labeled with various iodine radioisotopes, such as $^{124}$I, which can be easily detected by microPET, or $^{125}$I or $^{131}$I. Tissue distribution in murine tumor models has revealed high % injected dose/tumor ratios.

The goal of these experiments is to quantitate lesion uptake by microPET and tissue distribution studies. MicroPET images will be correlated anatomically with microCT scans obtained on a high-resolution microCT scanner and with histopathology.

Methods

Quantification of uptake of $^{124}$I-NM404 will be evaluated in LS-180 human colorectal cancer in SCID mice using micro PET images compared to autopsy specimens.

SCID mice will be injected with $10^6$ LS-180 cells subcutaneously in the right and left flank. This routinely results in tumor within 3 weeks of injection. Once tumors reach 5 mm in diameter, mice will be injected with 100 μCu of $^{124}$I-NM404. Because background levels are high in the first few days after injection, mice will be imaged for several consecutive days. microPET images will be obtained at 1, 2, and 4 days after injection. In order to co-register the images for attenuation correction so as to accurately quantify uptake, microCT will be performed on these days as well. After 7 days, animals will be euthanized and tumor sites identified as positive on microPET will be harvested for histological analysis, which will serve as the gold standard. Tumor size (using calipers) will be recorded at the time of harvest.

In this series of experiments, 10 tumor-bearing animals may be compared to 10 normal animals. Using 10 animals in each group will provide an 80% chance (power) for detecting as significant a 1.4 standard deviation shift (SDS) in the amount of NM404 at post-injection day 7 between the two groups. Quantification of microPET will be correlated with TD as shown below.

Tissue distribution studies using $^{125}$I-NM404 in a LS-180 human colorectal cancer model will be performed to quantitate uptake of NM404 and compare to quantification of microPET images.

Although it is possible to perform tissue distribution (TD) studies using $^{124}$I, this isotope is extremely expensive and would require large doses for TD studies. Thus, TD in animals may be performed with $^{125}$I-NM404, an isotope.

Biodistribution studies will be performed in female mice according to the standard procedure. Tumor will be established by subcutaneous injection of LS-180 cells. Once a 5 mm$^2$ diameter tumor is present, radioiodinated NM-404 (1 μCu/gm body weight) will be administered via tail vein injection. At predetermined time points (1 hours, 6 hours, 24 hours, 48 hours, and 4 and 10 days), animals (5/time point) will be euthanized by exsanguination while under pentobarbital anesthesia. A total of 16 tissues including blood, plasma, adrenal glands, bladder, bone marrow, fat, heart, kidney, liver, lung, muscle, spleen, ovaries, skin, thyroid, and tumor will be excised, rinsed, and dissected free of extraneous tissue. Large organs will be minced and duplicate tissue samples will be weighed into tared gelatin capsules and placed in plastic tubes for isotope counting. Injection site and residual carcass radioactivity will also be determined in a well counter. These standard procedures have been utilized for many years in the laboratory under appropriate animal care and radiation safety approval. Tissue distribution tables will be generated by a computer program developed by the inventors, which produces decay-corrected tissue radioactivity concentration data on a percent injected dose/g, % kg dose, and percent injected dose/organ±SEM basis. At each time point, tumor-to-tissue ratios will be calculated based on a percent injected dose/gram of tissue basis.

TD results will be compared to attenuation-corrected quantification obtained from microPET images. Based on tumor-to-tissue ratios of NM-404 estimated at 3 hours, and 1, 3, 7, 14, and 21 days post-injection for 5 animals at each timepoint, with an 80% chance (power) for detecting as significant a 2.1 standard deviation shift (SDS) in NM404 ratio between any two days.

Other routine laboratory procedures include synthesis, radiolabeling, and formulation of NM404. Unlabeled NM404 may be formulated and Radioiodinated by an isotope exchange reaction in ammonium sulfate at 160° C. as is routinely performed in the Contrast Agent Development Lab. Following HPLC purification and evaporation of the solvents, radioiodinated NM404 is dissolved in absolute ethanol (50-500 μl) and Polysorbate-20 (0.1 μl/μg of compound). The ethanol is removed under vacuum and the residue dissolved in sterile water to give a final solution containing no more than 2-3% Polysorbate-20. End-product sterilization is achieved by filtration of the solution through a sterile 0.2 μm syringe filter into a sterile dose vial. Final radiochemical purity must exceed 97% before using in animals. Injection volumes are typically around 100 μl per mouse.

II. Evaluate the Mechanism of Selective Retention of NM404 in Human Colorectal Cancer Cell Lines.

Further, in order to evaluate the mechanism of selective retention of NM404 in human colorectal cancer cell lines, Human colorectal cancer cell lines including LS-180, HT-29, and DLD-1 may be evaluated for the presence of mRNA encoding phospholipase D (isoforms 1 and 2) using quantitative PCR. The quantity of phospholipase D mRNA is then compared to normal colon tissue. The presence of phospholipase D protein (isoforms 1 and 2) may be evaluated by Western blot. The activity of phospholipase D (isoforms 1 and 2) protein may be evaluated in these same cell lines and compared to normal liver tissue using a commercially available fluorescence assay kit. NM404 is selectively retained in tumor cells due to a defect in the function of phospholipase $D_1$, an enzyme present in normal cells that degrades phospholipases. This compound appears to be a substrate for phospholipase D but not phospholipase A or C based on preliminary data. Thus the mechanism of prolonged retention in the cell is likely due to a decrease in the breakdown of NM404 secondary to a defect in phospholipase D, either at the transcriptional or translational level. Evaluating these assays in human cells first will provide an opportunity to refine the assays and also determine the potential relevance of $PLD_1$ vs. $PLD_2$, in order to apply this technology to human tissues.

Human colorectal cancer cell lines including LS-180, HT-29, and DLD-1 will be evaluated for the presence of mRNA encoding phospholipase D (isoforms 1 and 2) using quantitative PCR. Quantity of phospholipase D mRNA will be compared to normal colon tissue.

Single cell suspensions of LS-180, HT-29, and DLD-1 cell lines will be compared to homogenized normal colon tissue. mRNA will be purified using a commercially available kit (Qiagen, Inc), and 5 μg of total RNA will be converted to cDNA using reverse transcriptase (Promega). cDNA will be quantitated using a spectrophotometer and 10 ng of cDNA will be amplified by real-time PCR under the following conditions: (94° C., 30 sec; 65° C., 30 sec; and 72° C., 30 sec) for 50 cycles (iCycler, iQmix, Bio-Rad). The following primers will be used:

PLD1 (sense) 5'-ATTCGTTGGAGGTTGGACTG-3' SEQ ID NO. 1 (antisense) 5'-GTGCTGTCAATGCTGCTGAT-3' (Product 560 bases pairs) SEQ ID NO. 2

PLD2, (sense) 5'-CAGCAGGGACTCTGGAGAAC-3', SEQ ID NO. 3 (antisense) 5'-GGATGGTTCCGTCTCT-GTGT-3' (Product 557 bp) SEQ ID NO. 4

Product will be compared to a standard cDNA (GAPDH, Biosource International) diluted from 1 μg to $10^{-7}$ μg. Quantitative PCR is based on detection of a fluorescent product that is proportionally increased with amplification of the PCR product, thus allowing real-time assessment of the quantity of DNA product compared to control DNA.

The presence of phospholipase D (isoforms 1 and 2) will be evaluated by Western blot. Samples will be adjusted into gel loading buffer (125 mM Tris-HCL [pH 6.8], 4% sodium dodecyl sulfate [SDS], 0.1% bromophenol blue, 300 mM β-mercaptoethanol) and then heated for 3 min at 100° C. prior to separation by SDS-polyacrylamide gel electrophoresis (4-20% polyacrylamide gel). After transfer to a nitrocellulose membrane, using the Bio-Rad protein transfer system, the membrane will be blocked with 5% nonfat dry milk in a tris-buffered saline with 0.1% Tween 20 (TTBS). The membrane will then incubated with primary antibody either PLD1, PLD2, or GAPDH (Abcam), then treated with anti-rabbit IgG conjugated with horseradish peroxidase. Proteins bound to antibodies will be visualized with the SuperSignal West Femto Maximum Sensitivity Substrate (Pierce). To semi-quantitatively evaluate the level of PLD protein, the level of control PLD (in normal tissue) will be set at 100% and compared to tumor PLD, thus resulting in a relative fraction of tumor PLD/normal tissue PLD.

The activity of phospholipase D protein will be evaluated in these same cell lines and compared to normal liver tissue using a commercially available kit. The Amplex Red Phospholipase D Assay kit (Molecular Probes, Inc., Eugene, Oreg.) will be used to evaluate PLD activity, comparing single cell suspensions of LS-180, HT-29, DLD-1, and normal liver cells. Total protein will be extracted using a detergent solution (Triton-X-100) and quantity of PLD will be compared to a standard positive control. PLD activity will be assessed using an enzyme-coupled reaction. PLD activity will then be quantitated using a fluorescence microplate reader.

III. Evaluate the Mechanism of Selective Retention of NM404 in Human Colorectal Cancer Tissue.

Finally, in order to evaluate the mechanism of selective retention of NM404 in human colorectal cancer tissue, Human colorectal tissues (harvested at the time of initial colorectal resection or at the time of metastasectomy) will be evaluated for the presence of mRNA encoding phospholipase D (isoforms 1 and 2) using quantitative PCR. Quantity of phospholipase D mRNA will be compared to normal colorectal or liver tissue. The presence of phospholipase D (isoforms 1 and 2) will be evaluated by Western blot. The activity of phospholipase D (isoforms 1 and 2) protein will be evaluated in these same cell lines and compared to normal liver tissue using a commercially available fluorescence assay kit. NM404 is selectively retained in tumor cells due to a defect in the quantity or function of phospholipase $D_1$, an enzyme present in normal cells that degrades phospholipases. Ultimately, the most relevant study of the mechanism of NM404 is on human tissues. However, the difficulty in evaluating mRNA or protein in human tissue is that other cell types (with normal amounts of the targeted mRNA or protein) contaminate the evaluated specimens. Thus it is ideal to study the mechanism in human cells first, and to utilize laser capture microdissection of human tissues prior to performing quantititative PCR.

Human colorectal tissues (harvested at the time of initial colorectal resection or at the time of metastasectomy) will be evaluated for the presence of mRNA encoding phospholipase D (isoforms 1 and 2) using quantitative PCR. Quantity of phospholipase D mRNA will be compared to normal colorectal or liver tissue.

In order to decrease the chance of a false reading due to the presence of other adventitial cells and the marked amplification effect of PCR, laser capture microdissection on tissue samples will be first performed in order to capture tumor cells only for mRNA analysis. Once 1000 cancer cells are captured, quantititative PCR will be performed as described above. A total of 20 samples will be evaluated and compared to the patient's normal colorectal tissue.

The presence of phospholipase D (isoforms 1 and 2) will be evaluated by Western blot. Samples will be adjusted into gel loading buffer (125 mM Tris-HCL [pH 6.8], 4% sodium dodecyl sulfate [SDS], 0.1% bromophenol blue, 300 mM β-mercaptoethanol) and then heated for 3 min at 100° C. prior to separation by SDS-polyacrylamide gel electrophoresis (4-20% polyacrylamide gel). After transfer to a nitrocellulose membrane, using the Bio-Rad protein transfer system, the membrane will be blocked with 5% nonfat dry milk in a tris-buffered saline with 0.1% Tween 20 (TTBS). The membrane will then incubated with primary antibody either PLD1, PLD2, or GAPDH (Abcam), then treated with anti-rabbit IgG conjugated with horseradish peroxidase. Proteins bound to antibodies will be visualized with the SuperSignal West Femto Maximum Sensitivity Substrate (Pierce). To semi-quantitatively evaluate the level of PLD protein, the level of control PLD (in normal tissue) will be set at 100% and compared to tumor PLD, thus resulting in a relative fraction of tumor PLD/normal tissue PLD.

The activity of phospholipase D (isoforms 1 and 2) protein will be evaluated in these same cell lines and compared to normal liver tissue using a commercially available kit. The Amplex Red Phospholipase D Assay kit (Molecular Probes, Inc., Eugene, Oreg.) will be used to evaluate PLD activity, comparing single cell suspensions of LS-180, HT-29, DLD-1, and normal liver cells. Total protein will be extracted using a detergent solution (Triton-X-100) and quantity of PLD will be compared to a standard positive control. PLD activity will be assessed using an enzyme-coupled reaction. PLD activity will then be quantitated using a fluorescence microplate reader.

Generally, one approach to the development of sensitive, more available imaging exams is to design carrier molecules which are capable of selectively delivering a radiopharmaceutical probe to the desired target tissue. The inventors' approach has been to capitalize on the unique biochemical and pharmacological properties of phospholipid ether analogues such as NM404, which display a high degree of tumor selectivity. Phospholipids are an essential component of biological membranes, where they are present in the form of a lipid bilayer. Structurally, they have a glycerol backbone to which long chain fatty acyl groups and a phosphorylated moiety are affixed. Phosphatidylcholine, commonly known as lecithin, is such an example. Phospholipid ethers, on the other hand, represent a minor subclass of phospholipids that also reside in membranes. As the name implies, these lipids have an ether rather than an ester linkage at the C-1 position. Platelet-activating factor (PAF) represents one of the better known phospholipid ethers.

Snyder, et al, initially observed that animal and human tumors contained much higher concentrations of naturally occurring ether lipids in the cell membrane than normal tissue. He proposed that the accumulation of ether lipids in tumors arose as a result of a lower capacity of tumor cells to metabolize these lipids. The prevailing hypothesis (FIG. 2) is that phospholipid ethers become trapped in tumor membranes because of their inability to undergo metabolism and elimination, likely by a phospholipase in the cell membrane. This hypothesis is supported by experiments showing that extraction of tumors following administration of radioiodinated phospholipid ethers revealed only the intact agent, whereas analysis of urine and feces revealed only metabolites. Therefore, the hypothesis is that the reason tumors retain PLE is because of the differential clearance rates of PLE from normal cells versus tumor.

Extensive structure activity relationship studies resulted in the synthesis, radiolabeling, and evaluation of over 20 phospholipid ether analogs as potential tumor-selective imaging agents. Phospholipid ethers can easily be labeled with iodine radioisotopes using an isotope exchange method developed by Dr. Jamey Weichert. An important aspect of the construction of these phospholipid ether analogs is that they are specifically designed so that the radioiodine affixed to each molecule is stable to facile in vivo deiodination. In addition, during the original synthesis of these compounds, it was found that any chemical modification of the phosphocholine moiety or shortening of the chain length of the iodophenylalkyl moiety to less than 8 methylenes resulted in little or no tumor uptake.

Figure 3:
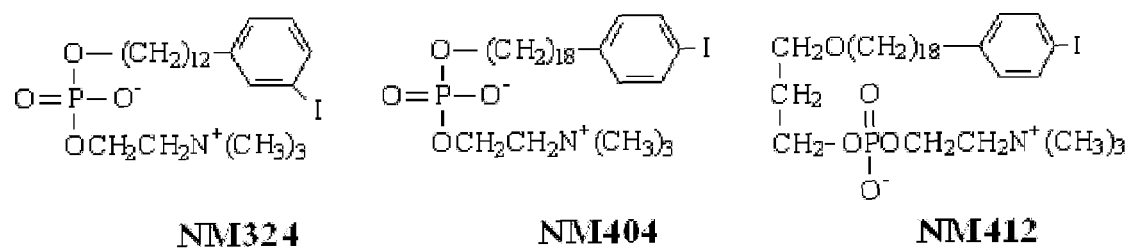
FIG. 3. depicts structures of PLE analogs.

In studies performed over the past several years over 20 radiolabeled phospholipid ether compounds have been synthesized and tested in vitro and in vivo. Two PLE analogs, namely NM294 and NM324 [12-(3-iodophenyl)-dodecylphosphocholine], initially showed the most promise in animal tumor localization studies, as seen in FIG. 3. Amazingly, many tumor types including mammary, prostate, squamous cell carcinoma, ovarian, colorectal, and melanoma were successfully visualized by scintigraphy with both $^{125}$I-PLE analogs. Although NM324 and NM294 displayed similar animal tumor localization patterns, NM324 was more readily synthesized and was thus selected as the lead compound for initial studies (FIG. 3).

These phospholipid ethers undergo facile radioiodination using an isotope exchange method. The iodophenyl phospholipid ether analogs are specifically designed so that the radioiodine affixed to each molecule is stable to facile in vivo deiodination, which is important in considering the applications for imaging as proposed.

While initiating human pharmacokinetic studies with the prototype agent, NM324, ongoing experiments to identify PLE compounds with superior tumor localization and background clearance properties were performed. Based upon this work, NM404 [12-(4-iodophenyl)-octadecylphosphocholine] was selected due to its enhanced ability to localize in tumor, its increased metabolic clearance from the liver, and its long plasma half life. In a key experiment documenting the ability of NM404 to localize to metastases, lymph node metastases were clearly delineated by scintigraphy in a metastatic prostate tumor model following intravenous administration of NM404, but the tracer was not retained by uninvolved lymph nodes.

Figure 4:
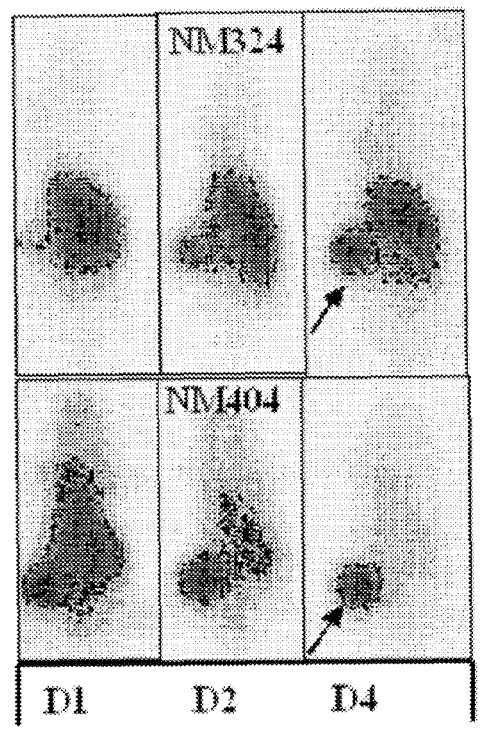
FIG. 4. depicts scintigraphic comparison of NM404 (bottom panel) and NM324 (top panel) at 1, 2, and 4 days in a SCID mouse with human prostate PC-3 tumor (arrow) implanted in the flank. Liver and background radioactivity are much improved with NM404.

Comparative scintigraphic imaging results for NM324 and NM404 in PC-3 prostate tumor-bearing SCID mice revealed high tumor-to-normal tissue ratios and significant decreases in background abdominal and liver radioactivity with NM404 (FIG. 4).

Figure 5:
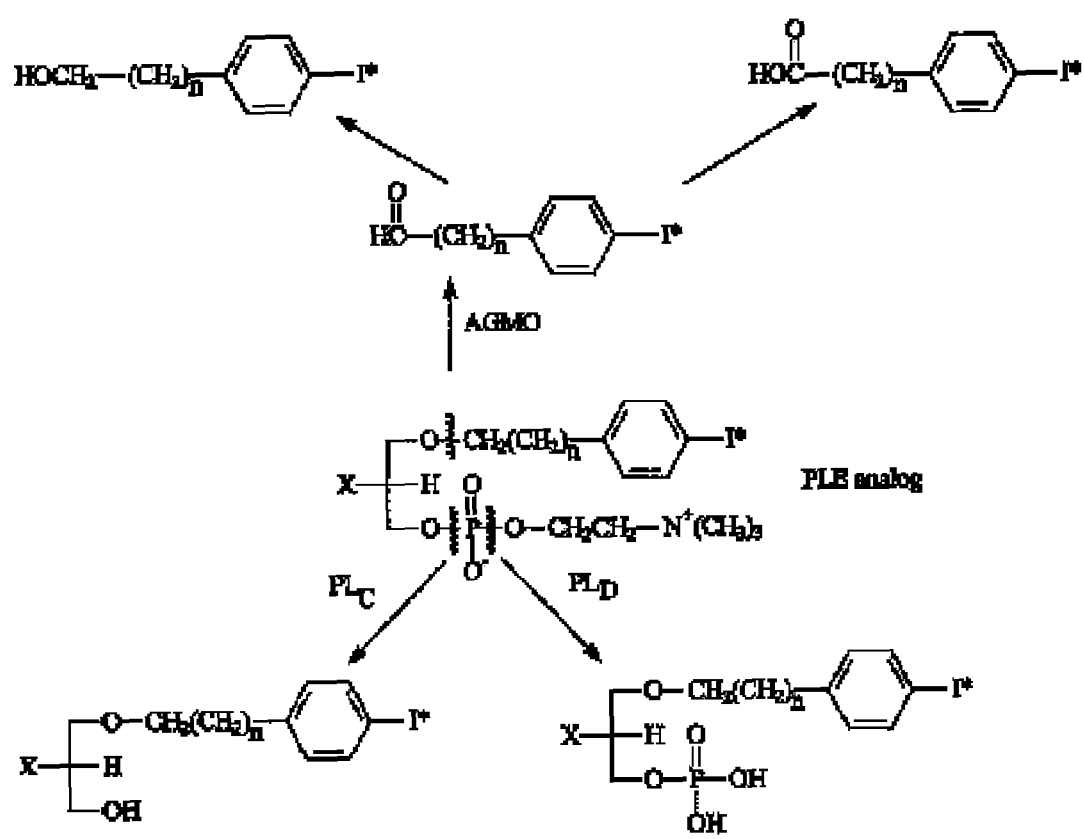
FIG. 5 depicts three major enzymatic pathways are involved in the metabolism of PLE. O-Alkyl glycerol monooxygenase (AGMO) is responsible for cleavage of the alkyl ether linkage at C-1 to form either the long chain fatty alcohol or subsequently the corresponding fatty acid. Phospholipases C (PLC) and D (PLD), on the other hand, give rise to the glycerol or phosphatidic acid products, respectively.

Mechanistic Studies with PLE Analogs:

Formal metabolism studies were conducted on several PLE analogs including NM324, the predecessor of NM404. In these studies, both agents were examined to determine their ability to serve as substrates for enzymes associated with PLE metabolism. Three major enzymatic pathways are involved in the metabolism of PLE. O-Alkyl glycerol monooxygenase (AGMO) is responsible for cleavage of the alkyl ether linkage at C-1 to form the long chain fatty alcohol. Phospholipases C (PLC) and D (PLD), on the other hand, give rise to the glycerol or phosphatidic acid products, respectively (FIG. 5). Using a microsomal AGMO enzyme preparation, NM324 was not a substrate for this enzyme when compared to [$^3$H]-lyso-PAF (platelet activating factor), which was extensively metabolized. In a similar fashion, NM324 was analyzed as a substrate for PLC isolated from *Bacillus cereus* and was not hydrolyzed relative to 1-palmitoyl-2-[3H]-palmitoyl-L-3-phosphatidylcholine (DPPC), which underwent significant hydrolysis. Thus it is likely that PLC is not responsible for the cleavage of this PLE analog.

Finally, several PLE analogs were subjected to a PLD assay. The PLD, which was isolated from cabbage, is similar to mammalian PLD in that the cabbage form affords phosphatidylethanol-type products in addition to phosphatidic acid when the enzymatic reaction is performed in the presence of ethanol. Several of the PLE analogs subjected to these assay conditions indeed generated phosphatidylethanol products, indicating that they were probable substrates for PLD. These studies, however, evaluated crude estimates of PLD activity and did not allow precise quantitation.

Several NM404 precursors were also subjected to in vitro metabolism studies in various cell lines including Walker tumor cells, rat muscle (H9c2), and rat hepatocytes. In these studies, the extent of metabolism was determined on the basis of radiolabeled products formed after incubation for various time periods and the results normalized to cell number or the amount of cellular protein. Subsequent lipid extraction of the incubation medium and cell suspension demonstrated little generation of PLE metabolites in the Walker tumor cells whereas a significant production of metabolites was seen in both the muscle cells and hepatocytes (normal, non-cancerous cells) over 48 hours. These results correlate nicely with in vivo biodistribution studies completed on all analogs. Although several studies have been completed, the role of metabolic trapping in the uptake and retention of radiolabeled PLE analogs in tumor cells is not well defined and currently remains an active area of examination.

Clinical Evaluation of NM324:

Of several promising first generation PLE analogs, NM324 was simpler to chemically synthesize and was thus selected as the lead compound for initial clinical studies. Although images obtained in 5 human lung cancer patients detected tumors, images were complicated by high liver radioactivity, thus NM404 was identified as the most promising PLE analog for clinical applications.

Second Generation PLE Analogs:

In order to decrease the high first-pass hepatic uptake and prolong the plasma half-life, 9 structural analogs of NM324 were synthesized and radiolabeled with $^{125}$I for initial image analysis in Copenhagen rats bearing Dunning R3327 prostate tumors. Based upon this initial screen, three analogs including NM404 were selected to undergo further imaging and biodistribution analysis in animal-tumor models. More recent imaging studies with NM404 in animal models showed that it is superior to NM324 in visualizing a variety of tumors (FIG. 4). Significantly, lymph node metastases were clearly delineated in a metastatic prostate tumor model following intravenous administration of NM404. Most importantly, the tracer was not retained by uninvolved lymph nodes. Although conducted in a prostate cancer model, this finding is particularly relevant since lymph node involvement is such an important prognostic indicator in many tumors. A pilot study conducted in SCID mice bearing human A549 non-small cell lung cancer was encouraging and demonstrated that NM404 overcomes the problem of high first pass clearance of NM324 by the liver. NM404 showed excellent tumor visualization, especially striking in the delayed images, with minimal liver and kidney uptake in comparison with NM324. Comparative biodistribution data for NM324 and NM404 in SCID mice with prostate and A549 lung cancer tumor models have revealed high tumor to normal tissue ratios and tumor uptake exceeding 25% of the injected dose with NM404.

Biodistribution Data

Extensive biodistribution data for the prototype agent $^{125}$I-NM324 in several tumor models have previously been compiled. Tumor-to-blood ratios exceeding 8:1 were seen at delayed times post-injection. For example, in a rat mammary tumor model, tumor-to-normal tissue ratios reached a maximum at 96 hours with a tumor-to-blood ratio of 8.6 and tumor-to-muscle ratio of 20:1. Moreover, the biodistribution of PLE-associated radioactivity is heterogeneous in tumor, as demonstrated by microautoradiography studies showing that the PLE radioactivity resides exclusively in viable tumor cells located toward the outer regions rather than the central necrotic regions. Comparative biodistribution data for NM324 and NM404 in SCID mice have been performed in prostate and A549 lung cancer tumor models. These studies revealed high tumor-to-normal tissue ratios and tumor uptake exceeding 25% of the injected dose with NM404.

Significance

Because of what appears to be a near-universality of selective retention of NM404 for multiple tumor types, there are widespread implications for imaging and/or treating human tumors. The most exciting aspect of this work includes the fact that NM404 seems to be retained by so many different tumor types, thus resulting in a potential common agent that could image and/or treat multiple tumor types. These experiments will further define the mechanism of this effect, and may enable to differentiate a tumor cell phenotype that for predicting the sensitivity to radiolabeled NM404 for both imaging and therapeutic applications. These findings have the potential to greatly impact the clinical care of cancer patients, with implications for early detection of tumor in high-risk groups, staging tumors at the time of initial presentation prior to surgical resection, and following patients for recurrence after surgery. Perhaps even more exciting is the possibility that $^{131}$I-NM404 could have therapeutic applications for various cancer histologies.

Although this agent is being studied in human clinical trials of lung cancer, the understanding of the mechanism of uptake is still not entirely defined.

Other Tumor Studies:

Phospholipid ether analogs have now been evaluated in multiple implanted and spontaneously arising animal tumor models. It is clear that once the agent enters tumor cells, it reaches a metabolic dead end and becomes trapped. Using $^{125}$I-labeled NM404, the inventors have been able to image mammary and prostate tumors in mice in excess of 60 days. Recent imaging studies performed in mouse models are summarized in Table 1. NM404 has displayed significant tumor uptake and retention in every adenocarcinoma model studied.

TABLE 1

Summary of tumor models examined with radiolabeled phospholipids ethers.

| | Type | Uptake and Retention |
|---|---|---|
| Human Tumor Xenografts | | |
| Prostate PC-3 | Adenocarcinoma | Yes |
| Lung A-549 (NSSLC) | Adenocarcinoma | Yes |
| Lung H-69 (Oat Cell) | Adenocarcinoma | Yes |
| Adrenal H-295 | Adenocarcinoma | Yes |
| Adrenal RL-251 | Adenocarcinoma | Yes |
| Melanoma A-375 | Adenocarcinoma | Yes |
| Colon LS-180 | Adenocarcinoma | Yes |
| Ovarian HTB-77 | Adenocarcinoma | Yes |
| Rat Xenografts | | |
| Mammary MCF7 | Adenocarcinoma | Yes |
| Prostate MatLyLu | Adenocarcinoma | Yes |
| Walker-256 | Carcinosarcoma | Yes |
| Recent Rodent Models | | |
| TRAMP/LuCAP Prostate | Adenocarcinoma | Yes |
| Colon CT-26 or Colon-51 | Adenocarcinoma | Yes |
| Mammary APCMin | Squamous Cell Carcinoma | Yes |
| Mammary APCMin | Adenocarcinoma | Yes |
| Liver HCC-TGFα | Adenocarcinoma | Yes |
| Glioma-L9/CNS-1 | Glioma | Yes |
| Squamous Cell 1 and 6 | Squamous Cell Carcinoma | Yes |
| Pancreatic c-myc/kras | Adenocarcinoma | Yes |
| Retinoblastoma | Blastoma | Yes |
| Cervical | Adenocarcinoma | Yes |
| ApcMin Mammary hyperplasia | Alveolar Hyperplasia | No |
| ApcMin Intestinal polyp | Adenomatous Polyp | No |

Isotope Selection

Because the tumor-targeting strategy of PLE analogs appears to involve selective tumor retention over time (several days), relatively short-lived nuclides such as $^{18}$F or even $^{99m}$Tc are not practical for labeling NM404. However, it is highly advantageous to label PLE analogs with iodine-124, a relatively new PET isotope which has just become commercially available. This isotope is ideal for labeling NM404 because its physical half-life (4 days) matches well with PLE tumor uptake and retention kinetics. $^{124}$I has a complex decay scheme with about 23% disintegrations resulting in positron emissions, thus imaging with PET is possible.

This is important because PET imaging with $^{124}$I affords over 40 times the sensitivity of planer (2-dimensional) $^{131}$I-gamma imaging because of increased resolution enhancement and its 3-dimensional capabilities. As compared to the common short-lived PET radionuclides such as $^{18}$F-FDG, $^{124}$I is a long half-life radionuclide. Thus, it is suitable as a tracer to monitor events which occur over days as opposed to minutes or hours. The decay half-life of iodine combined with the quantitative capability of PET imaging makes it an attractive option to study processes which occur over days. While still in its infancy, the applications of $^{124}$I PET studies are growing. While $^{131}$I-NM404 gamma scinitigraphy has been found to be useful in a variety of cancers in animal tumor models (Table 1), $^{124}$I-NM404 PET imaging could potentially offer significant advantages over $^{131}$I-NM404. Firstly, PET imaging is inherently more sensitive than gamma scintigraphy. Secondly, higher spatial resolution can be obtained with PET imaging than with gamma scintigraphy or SPECT scanning. Thirdly, absolute quantitation of tissue activity and tracer kinetic analysis are more accurate with PET imaging. Finally, because of better quantitation, there is likely less variability between imaged subjects with PET imaging than with gamma scintigraphy.

Unfortunately, iodine-124, although extremely promising for tumor-selective imaging with PET, has only been commercially available for a short time. Preliminary work has shown that it is possible to radioiodinate NM404 with $^{124}$I, although the process has not yet been optimized for maximal radiochemical yield. Labeling NM404 with iodine-124 to determine its tumor detection efficacy with 3-dimensional PET images is desirable because of the limitations in accuracy of imaging with 2-dimensional SPECT images utilizing $^{131}$I.

The utility of currently available tracers (e.g. $^{67}$Ga and $^{18}$F-FDG) is limited by lack of specificity to distinguish neoplasm from inflammation, which is a significant clinical issue in patients with cancer. However, preliminary studies with PLE analogs offers promise in overcoming this clinically significant limitation. Prior experiments revealed that in rats with carrageenan-induced granulomas, there was no visualization above background activity in these inflammatory lesions, and there was no tissue retention when NM404 was evaluated. Gallium citrate, however, which was utilized as a control in that study, did concentrate significantly in the granulomatous lesions. Thus, the finding that PLE analogs do not localize to inflammatory lesions further justifies the need for evaluation of this agent for imaging cancer.

Imaging Results in CT-26 Murine Tumor Model

Figure 6:
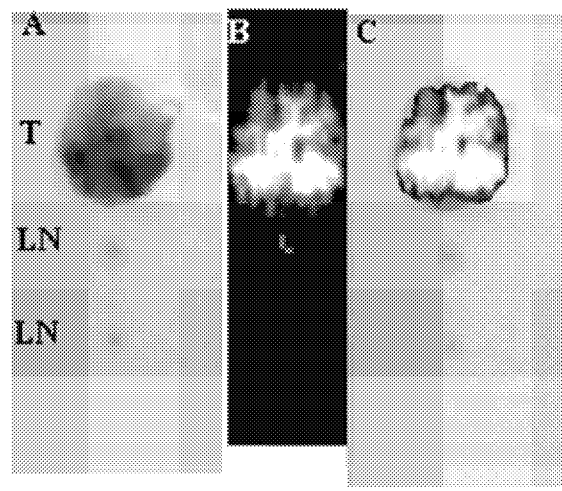
FIG. 6 depicts digital Photo (A) of excised CT-26 tumor (T) and left and right lymph nodes (LN). Bioscan image (B) and fused photo/Bioscan image (C) showing correlation of radioactivity in tumor but not in benign nodal tissue.

Current experiments explore the use of NM404 for imaging colorectal cancer in a human colorectal cancer cell line implanted in SCID mice. The inventors have previously shown that a murine colorectal cell line, CT-26, implanted in syngeneic Balb/C mice, can be successfully imaged with $^{125}$I NM404 (10 μCi injected via tail vein, FIG. 6). Ex vivo scanning, as was used here, is a standard protocol in these experiments due to the severe tissue attenuation effects associated with iodine-125. Animals were imaged on a modified Bioscan AR2000 radio TLC scanner (equipped with high resolution 1 mm collimator and 2-D acquisition and analysis software).

Evaluation of PLD mRNA and Protein Activity in Murine Tumor Models

Due to the apparent universality of tumor retention of NM404, the inventors began to investigate the mechanism of uptake of this agent more systematically. Although membrane metabolism of PLE analogs is regulated by a variety of phospholipases, initial efforts were focused on phospholipase D (PLD) activity, based on the hypothesis that uptake and retention is inversely related to the amount of PLD present in the tumor cell membrane relative to normal cells. Because of these findings, evaluation of PLD protein activity and mRNA quantity were performed in murine tumor cell lines, including the murine tumor cell line hepa-1 (hepatoma), CT26 (colorectal adenocarcinoma), and TS/A (breast adenocarcinoma) and compared to normal liver. These experiments revealed that both PLD protein activity and mRNA levels were significantly lower in tumor than in normal liver tissue (p<0.05, T-test, Table 2). Therefore, the mechanism of selective retention of NM404 may be due to a decrease in the membrane levels of PLD, thus precluding metabolism and clearance of NM404 from the cell.

TABLE 2

PLD protein activity and mRNA levels in murine tumor models.

| Cell/tissue | PLD protein activity (mU/fluorescence/μg protein/ml) | PLD mRNA (μg × 10$^{-5}$/0.01 μg of total cDNA) |
|---|---|---|
| Hepa-1 | 3.3 | 6.2 |
| CT26 | 7.8 | 2.4 |
| TS/A | 2.8 | 4.0 |
| Normal liver | 14.1 | 12.2 |

Generally, a tumor with the lowest levels of PLD activity will be the most amenable to treatment with radiolabeled NM404.

Animal/power Analysis

Power calculations for animal experiments were based on the desire to detect a difference between two groups using a t-test. In the experiments described under specific aim #1A, with 10 animals per group, the inventors will have an 80% chance (power) for detecting as significant a 1.4 standard deviation shift between two groups. Accordingly, with five animals per group, there is an 80% chance (power) for detecting as significant a 2.1 standard deviation shift between two groups. This is assuming that p-values less than 0.05 will be considered as significant.

Experimental Methodology:

Quantitative PCR in human colorectal cancer cell lines shows decreased expression of PLD1 and PLD2 compared to normal cells.

Experimental.

Human colorectal cancer cell lines including LS-180, HT-29, and DLD-1 were evaluated for the presence of mRNA encoding phospholipase D (isoforms 1 and 2) using quantitative PCR. Quantity of phospholipase D mRNA was compared with the human normal colon cell line CCD-18co.

mRNA was isolated from single cell suspensions for all four cell lines using a commercially available kit (Qiagen, Inc), and 5 μg of total RNA converted to cDNA using reverse transcriptase (Promega). 10 ng of cDNA was amplified initially by Hot-Start PCR using a set of primers to give PCR products of 560 bp for $PLD_1$ and 557 bp for $PLD_2$ under the following PCR conditions: 3 min denaturation at 94° C. followed by 50 cycles of denaturation at 94° C. for 30 sec, annealing at 65° C. for 30 sec and elongation at 72° C. for 30 sec. For quantitative PCR, 10 ng of the PCR products were then subjected to a final amplification of 50 cycles by real-time PCR using SYBR Green as the fluoroprobe under the following conditions: (94° C., 30 sec; 65° C., 30 sec; and 72° C., 30 sec) for 50 cycles (iCycler, iQmix, Bio-Rad).

Products were compared with a standard cDNA similarly amplified for the housekeeping gene S26, (Biosource International) diluted from 1 μg to $10^{-7}$ μg. Quantitative PCR is based on detection of a fluorescent product that is proportionally increased with amplification of the PCR product, thus allowing real-time assessment of the quantity of DNA product compared with control DNA.

Results:

Table 3. is a summary of the results.

TABLE 3

QPCR RESULTS FOR PLD1 & PLD2 MESSAGES IN THE HUMAN NORMAL COLON AND 3 ADENOCARCINOMA CELL LINES.

| | CELL LINE: | | | | |
|---|---|---|---|---|---|
| | CCD-18co | DLD-1 | HT-29 | LS-180 | Value |
| PLD-1. | | | | | |
| I | 2.79 | 3.41 | 4.03 | 3.06 | $\times 10^2$ |
| II | 3.54 | 5.25 | 5.49 | 3.45 | " |
| S26 | | | | | |
| I | 1.21 | 2.01 | 1.31 | 2.61 | $\times 10^6$ |
| II | 1.73 | 2.15 | 2.27 | 3.28 | " |
| PLD-1/S26 | | | | | |
| I | 2.31 | 1.70 | 3.08 | 1.17 | $\times 10^{-4}$ |
| II | 2.05 | 2.44 | 2.42 | 1.05 | " |
| Average: | 2.18 ± 0.13 | 2.07 ± 0.37 | 2.75 ± 0.33 | 1.11 ± 0.06 | |
| Ratio: Normal to tumor (CCD/Tumor Cell Line) | | | | | |
| I | 1.0 | 1.35 | 0.75 | 1.96 | |
| II | 1.0 | 0.84 | 0.85 | 1.95 | |
| Average: | | 1.10 ± 0.25 | 0.80 ± 0.05 | 1.96 ± 0.01 | |
| PLD-2 | | | | | |
| I | 3.32 | 1.59 | 0.54 | 0.32 | $\times 10^2$ |
| II | 4.92 | 3.12 | 0.88 | 0.39 | " |
| S26 | | | | | |
| I | 1.10 | 1.14 | 1.26 | 1.87 | $\times 10^6$ |
| II | 2.58 | 2.51 | 2.33 | 4.51 | " |
| PLD-2/S26 | | | | | |
| I | 3.02 | 1.39 | 0.43 | 0.17 | $\times 10^{-4}$ |
| II | 1.91 | 1.24 | 3.76 | 0.09 | " |
| Average: | 2.47 ± 0.56 | 1.32 ± 0.08 | 2.10 ± 1.66 | 0.13 ± 0.04 | |
| Ratio: Normal to tumor (CCD/Tumor Cell Line) | | | | | |
| I | 1.0 | 2.17 | 7.14 | 16.95 | |
| II | 1.0 | 1.54 | 5.10 | 22.47 | |
| Average: | | 1.86 ± 0.32 | 6.12 ± 1.02 | 19.71 ± 2.76 | |

Units are in copy numbers of cDNA.

Conclusion from Results:

Inventors hypothesize that the likely mechanism for the prolonged retention of NM404 in tumors is a defect in an isoform of phospholipase D (PLD), an enzyme found in the cell membrane that is likely responsible for the breakdown and clearance of NM404 in normal cells. Therefore, the attached qPCR results demonstrating decreased expression of both isoforms of the phospholipase D gene (PLD1 and PLD2) in the tumor cell lines compared to the normal CCD-18co, provides further proof for, and strengthens this hypothesis implicating decreased PLD enzyme activity in the selective retention of NM404 in tumors. By understanding the mechanism of selective retention of NM404, specific tumor types may be better defined such that these specific tumors will be more sensitive to the effect of radiolabeled PLE analogs such as NM404, and resulting in improved imaging and/or therapy of these tumors.

Generally, in over 10 human and mouse tumor types examined by classical Amplex Red assay, PLD level in tumor cells was 2-10 fold less than normal host tissues. Further, utilizing laser capture micro-dissection to isolate only malignant cells from a human pancreatic tumor, the level of PLD-1 was found to be 275 fold less than surrounding normal host tissues Radiotherapeutic Study of I-125-NM404

Figure 8:
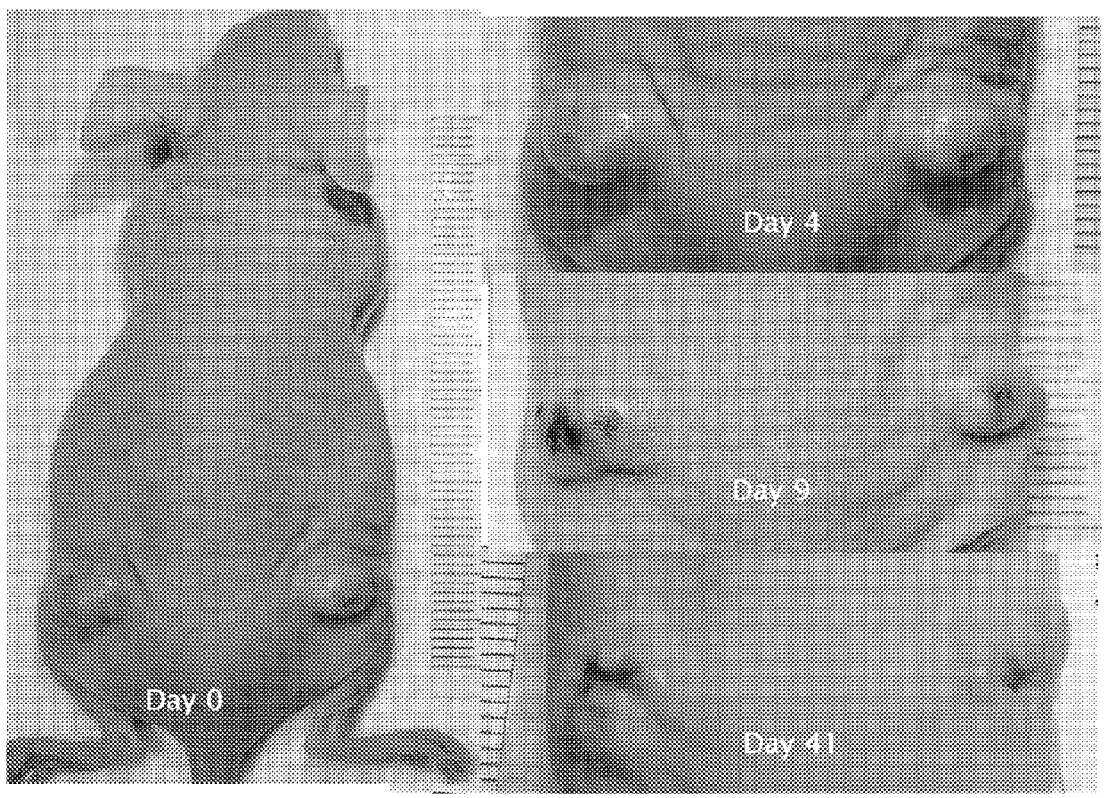
FIG. 8 depcits apparent SCC 1 and 6 tumor regression after injection of $^{125}$I-NM404. Treated mouse was euthanized at 90 days whereas untreated Sibling died at 21 days.

During the course of mouse tumor uptake and retention studies with "imaging" doses (15-20 μCi/20 g mouse) of $^{125}$I-labeled NM404, several apparent therapeutic responses have been observed (unpublished results). In an Apc$^{Min}$/+ mouse mammary tumor model it has generally been noted that tumor growth remains static following a single intravenous injection of NM404. Some of these animals also lost all hair above larger mammary tumors at around 8 days after injection. Moreover, these mice also get intestinal tumors and usually suffer from intestinal bleeding resulting in severe anemia, which renders their feet white. Dr. Moser noted that the feet of these mice had reverted to a pink color around 5 days after a single injection of NM404. Upon eventual dissection of these animals, it was noted that only a very few, if any, of the expected 20 or so intestinal tumors usually found at this age actually remained. The "white to pink feet" phenomenon was also observed in a separate, but more aggressive, mouse intestinal adenocarcinoma model, wherein dissection at 12 days following NM404 administration, again revealed that most, if not all, of the expected intestinal tumors were gone. After 21 days in both intestinal models, animals that received NM404 easily outlived their untreated litter mates. Another compelling example of tumor regression is illustrated in FIG. 8. Two litter mates each received SCC1 and SCC6 xenografts in their left and right flanks, respectively. One mouse received a single injection of $^{125}$I-NM404 (20 μCi). The mouse that didn't receive NM404 died 21 days later, whereas the tumors in the treated mouse regressed significantly and the animal was quite healthy 80 days after injection. These coincidental findings were reconfirmed in two separate age-matched groups each involving more than 6 mice. Although these observations with [125]I-NM404 are anecdotal at this point, they do seem to strongly indicate potential for radiotherapy applications particularly if labeled with iodine-131. Ongoing quantitative tumor uptake and retention studies in several animal tumor models will also provide sufficient data to initiate a comprehensive dosimetry analysis for this agent in order to estimate its true radiotherapeutic potential.

Due to its 60-day physical half-life and low energy 35 KeV photon emission, iodine-125 is suitable for imaging experiments in mice and rats. Iodine-125 also affords therapeutic characteristics. In one imaging experiment (FIG. 6), 2 nude mice were each inoculated with subcutaneous squamous cell lines SCC1 and SCC6 tumor cell implants on opposing flanks. SCC1 and SSC6 cells were used because one is radiosensitive relative to the other. After 14 days when the average tumor size was approaching 0.5 cm in diameter, one of the mice received 20 μCi of I-125-NM-404 and the other one receive unlabeled NM404 in an equal mass dose. The mouse receiving the unlabeled cold compound had to be euthanized 20 days after injection due to both tumors reaching the termination size limit as defined in the animal use protocol. Both tumors in the [125]I-NM404 mouse regressed dramatically and unexpectedly over the course of several weeks (FIG. 6) after a single injection of an imaging dose of NM404. This mouse never did reach terminal tumor size and the mouse was actually euthanized after 90 days in order to collect histology sections.

Additional details related to therapeutic use of the phospholipid compounds are provided in U.S. patent application Ser. No. 11/316,620 and PCT/US05/47657, both of which were filed on Dec. 20, 2005, and both of which are incorporated herein by reference for all purposes.

Thus present invention generally relates to imaging and selective retention of phospholipid ether analogs in various neoplastic tissues. Specifically, the present invention relates to imaging and methods for selective retention of analogs, for example, NM404, in cancers such as Colorectal Cancer. In one exemplary embodiment, the present invention provides a method of detecting neoplasia in a tissue sample from a patient having a phospholipase D (PLD) comprising the step of: (1) quantifying the PLD protein activity level or the PLD mRNA level in the tissue sample; and (2) determining whether the tissue sample has a lower level of protein activity than control or surrounding tissue region(s) wherein a lower activity region indicates detection and location of the neoplasia, or (3) determining whether the tissue sample has a lower level of mRNA than control or surrounding tissue region(s) wherein a lower mRNA level region indicates detection and location of the neoplasia. In this method the PLD protein activity or the mRNA level is quantified by quantitative PCR (QPCR).

Further, once the presence of the neoplastic tissue is determined then in this method, the patient having the lowered PLD protein activity level or the PLD mRNA is further administered with a PLE analog. This PLE analog is preferably selected from:

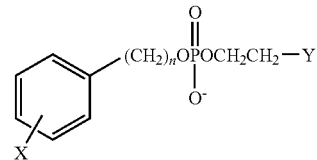

where X is selected from the group consisting of radioactive isotopes of halogen; n is an integer between 8 and 30; and Y is selected from the group comprising $NH_2$, $NR_2$, and $NR_3$, wherein R is an alkyl or arylalkyl substituent or

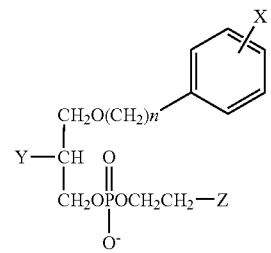

where X is a radioactive isotope of halogen; n is an integer between 8 and 30; Y is selected from the group consisting of H, OH, COOH, COOR and OR, and Z is selected from the group consisting of $NH_2$, $NR_2$, and $NR_3$, wherein R is an alkyl or arylalkyl substituent. In this method the administration of the PLE analog in the patient results in the treatment or reduction of said neoplasia in the patient.

As for the PLE compound used in this method, preferably, in the compound X is selected from the group of radioactive halogen isotopes consisting of $^{18}F$, $^{36}Cl$, $^{76}Br$, $^{77}Br$, $^{82}Br$, $^{122}I$, $^{123}I$, $^{124}I$, $^{125}I$, $^{131}I$ and $^{211}At$. More preferably, the phospholipid ether is 18-(p-Iodophenyl)octadecyl phosphocholine, 1-O-[18-(p-Iodophenyl)octadecyl]-1,3-propanediol-3-phosphocholine, or 1-O-[18-(p-Iodophenyl)octadecyl]-2-O-methyl-rac-glycero-3-phosphocholine, wherein iodine is in the form of a radioactive isotope.

Also in this method, the tissue having the PLD is isolated with laser capture microdissection prior to quantifying the PLD protein level activity or the PLD mRNA activity using QPCR. This method is useful in selectively removing neoplstic tissue from the surrounding tissue. Once the neoplastic tissue is separated, PLD levels are measured in this tissue and compared to the surrounding tissue or the control. Typically, the average ratio of PLD mRNA level in the control or the normal surrounding tissue to the neoplastic tissue is expected to about 1.1 to about 3000. Higher ratio makes the patient a better candidate for receiing therapy treatment using NM404 compound or other PLE analogs as described in this invention. Once the PLE analog is administered to the patient, it is further detected by PET, CT, MRI scanning methods and combination thereof. In a preferred embodiment, the neoplasia is selected from the group consisting of Lung cancer, Adrenal cancer, Melanoma, Colon cancer, Colorectal cancer, Ovarian cancer, Prostate cancer, Liver cancer, Subcutaneous cancer, Squamous cell cancer, Intestinal cancer, Hepatocellular carcinoma, Retinoblastoma, Cervical cancer, Glioma, Breast cancer, Pancreatic cancer and Carcinosarcoma.

In another exemplary embodiment, the present invention teaches methods for screening anti-tumor compounds using the PLD activity levels. In this methodology the fluorescent, luminescent or radiolabeled anti-tumor agent is selected by a method of screening a tissue sample from a patient having a PLD. The screening steps steps include the following: (i) contacting the anti-tumor agent with the tissue sample; (ii) detecting the selective retention of the anti-tumor agent in the tissue sample; (iii) quantifying the PLD protein activity or PLD mRNA level in the tissue sample, wherein reduced PLD protein activity or reduced mRNA level compared to control or surrounding tissue region(s) is indicative of a neoplasitic tissue; and (iv) determining whether the neoplastic tissue sample of step (iii) selectively retains the anti-tumor agent by comparing the anti-tumor agent retention in the control or the surrounding tissue region(s) to the retention in the neoplastic tissue sample wherein a lower retention in the control or the surrounding tissue as compared to the neoplastic tissue sample is indicative of tumor-selective anti-tumor compound.

Inventors believe that using this screening method which employs the mechanistic retention of PLE analogs in neoplastic tissues, other anti-tumor agents which have similar mechanistic pathway may also be discovered where lowered PLD levels allows for selective retention of these anti-tumor agents. In this method, the anti-tumor agent is detected by PET imaging, CT imaging, MRI imaging, fluorescence imaging, or combinations thereof. Hoever, other methodology known to one of ordinary skill in the art may also be used.

In yet another exemplary embodiment, the present invention provides a method of identifying a patient having neoplasia for receiving treatment with phospholipid analog of claim 3, comprising the steps of: (i) removing a tissue sample from a patient having a phospholipase D (PLD); (ii) quantifying the PLD protein activity level or the PLD mRNA level in the tissue sample, wherein a lower level of protein activity level or PLD mRNA level than control or surrounding tissue region(s) indicates detection and location of the neoplasia; and (iii) administering to the patient having a PLD mRNA ratio of about 1.1 to about 3000 in the control or the normal surrounding tissue to the neoplastic tissue with a PLE analog as described above. Inventors believe that this method can be used as an important screening method for determining and identifying which patients having neoplasia would be good candidates for receiving the PLE analog treatment.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES (1) Cancer Facts and Figures. American Cancer Society 2000. 2001. Ref Type: Generic
(2) Penna C, Nordlinger B. Colorectal metastasis (liver and lung). Surg Clin North Am 2002; 82:1075-10xi.
(3) Fong Y, Fortner J, Sun R L et al. Clinical score for predicting recurrence after hepatic resection for metastatic colorectal cancer: analysis of 1001 consecutive cases. Ann Surg 1999; 230:309-318.
(4) Ike H, Shimada H, Ohki S et al. Results of aggressive resection of lung metastases from colorectal carcinoma detected by intensive follow-up. Dis Colon Rectum 2002; 45:468-473.
(5) deGramont A, Vignoud J, Tournigand C et al. Oxaliplatin with high-dose leucovorin and 5-fluorouracil 48 hour continuous infusion in pretreated metastatic colorectal cancer. European Journal of Cancer 1997; 33:214-219.
(6) Hoffman D R, Hoffman L H, Snyder F. Cytotoxicity and metabolism of alkyl phospholipid analogues in neoplastic cells. Cancer Res 1986; 46:5803-5809.
(7) Scott C C, Heckman A, Nettesheim P et al. Metabolism of ether-linked glycerolipids in cultures of normal and neoplastic rat respiratory tract epithelium. Cancer Res 1979; 39:207-214.
(8) Plotzke K P, Fisher S J, Wahl R L et al. Selective localization of a radioiodinated phospholipid ether analog in human tumor xenografts. J Nucl Med 1993; 34:787-792.
(9) Weichert J P VdMGMCR. Radioiodination via isotope exchange in pivalic acid. IntJ Appl Rad Isotopes [38], 907-913. 1986. Ref Type: Generic
(10) Rampy M A, Brown R S, Pinchuk A N et al. Biological disposition and imaging of a radioiodinated alkylphosphocholine in two rodent models of breast cancer. J Nucl Med 1996; 37:1540-1545.
(11) Snyder F, Wood R. The occurrence and metabolism of alkyl and alk-1-enyl ethers of glycerol in transplantable rat and mouse tumors. Cancer Res 1968; 28:972-978.
(12) Rampy M A, Pinchuk A N, Weichert J P et al. Synthesis and biological evaluation of radioiodinated phospholipid ether stereoisomers. J Med Chem 1995; 38:3156-3162.
(13) Plotzke K P, Rampy M A, Meyer K et al. Biodistribution, metabolism, and excretion of radioiodinated phospholipid ether analogs in tumor-bearing rats. J Nucl Biol Med 1993; 37:264-272.
(14) Counsell R E, Longino M, Pinchuk A., Skinner S, Weichert J P. Synthesis and evaluation of radioiodinated phospholipid ethers for imaging of prostate cancer. Quart J Nucl Med 41, 14-16. 1997. Ref Type: Generic
(15) Plotzke K P, Haradahira T, Stancato L et al. Selective Localization of Radioiodinated Alkylphosphocholine Derivatives in Tumors. Nuclear Medicine and Biology 1992; 19:765-773.
(16) Rampy M A, Brown R S, Pinchuk A N et al. Biological disposition and imaging of a radioiodinated alkylphosphocholine in two rodent models of breast cancer. J Nucl Med 1996; 37:1540-1545.
(17) Pentlow K S, Graham M C, Lambrecht R M et al. Quantitative imaging of iodine-124 with PET. Journal of Nuclear Medicine 1996; 37:1557-1562.
(18) Barton J B, Langdale L A, Cummins J S et al. The utility of routine preoperative computed tomography scanning in the management of veterans with colon cancer. Am J Surg 2002; 183:499-503.
(19) Platell C F, Semmens J B. Review of survival curves for colorectal cancer. Dis Colon Rectum 2004; 47:2070-2075.
(20) Blasberg R G, Roelcke U, Weinreich R et al. Imaging brain tumor proliferative activity with [1-124]iododeoxyuridine. Cancer Research 2000; 60:624-635.
(21) Frey P, Townsend D, Jeavons A et al. Invivo Imaging of the Human Thyroid with A Positron Camera Using 1-124. European Journal of Nuclear Medicine 1985; 10:472-476.
(22) Ott R j, Batty V, Webb S et al. Measurement of Radiation-Dose to the Thyroid Using Positron Emission Tomography. British Journal of Radiology 1987; 60:245-251.
(23) Langen K J, Coenen H H, Roosen N et al. Spect Studies of Brain-Tumors with L-3-[1-123] Iodo-Alpha- Methyl Tyrosine—Comparison with Pet, 124Imt and 1St Clinical-Results. Journal of Nuclear Medicine 1990; 31:281-286.
(24) Snook D E, Rowlinsonbusza G, Sharma H L et al. Preparation and Invivo Study of 1-124 Labeled Monoclonal-Antibody H17E2 in A Human Tumor Xenograft Model—A Prelude to Positron Emission Tomography (Pet). British Journal of Cancer 1990; 62:89-91.
(25) Wilson C B, Snook D E, Dhokia B et al. Quantitative Measurement of Monoclonal-Antibody Distribution and Blood-Flow Using Positron Emission Tomography and 1-124 in Patients with Breast-Cancer. International journal of Cancer 1991; 47:344-347.
(26) Westera G, Reist H W, Buchegger F et al. Radioimmuno Positron Emission Tomography with Monoclonal-Antibodies—A New Approach to Quantifying Invivo Tumor Concentration and Biodistribution for Radioimmunotherapy. Nuclear Medicine Communications 1991; 12:429-437.
(27) Larson S M, Pentlow K S, Volkow N D et al. Pet Scanning of Iodine-124-3F8 As An Approach to Tumor Dosimetry During Treatment Planning for Radioimmunotherapy in A Child with Neuroblastoma. Journal of Nuclear Medicine 1992; 33:2020-2023.
(28) Bakir M A, Eccles S, Babich J W et al. C-Erb2 Protein Overexpression in Breast-Cancer As A Target for Pet Using Iodine-124I-Labeled Monoclonal-Antibodies (Journal of Nuclear Med, Vol 33, Pg 2154, 1992). Journal of Nuclear Medicine 1993; 34:290.
(29) Sundaresan G, Yazaki P J, Shively J E et al. $^{124}$I-labeled engineered anti-CEA minibodies and diabodies allow high-contrast, antigen-specific small-animal PET imaging of xenografts in athymic mice. J Nucl Med 2003; 44:1962-1969.
(30) Lee F T, Hall C, Rigopoulos A et al. Immuno-PET of human colon xenograft-bearing BALB/c nude mice using $^{124}$I-CDR-grafted humanized A33 monoclonal antibody. J Nucl Med 2001; 42:764-769.
(31) Blasberg R G, Roelcke U, Weinreich R et al. Imaging brain tumor proliferative activity with [1-124]iododeoxyuridine. Cancer Research 2000; 60:624-635.
(32) Counsell R E, Schwendner S W, Meyer K L et al. Tumor visualization with a radioiodinated phospholipid ether. J Nucl Med 1990; 31:332-336.
(33) Gali H, Sieckman G L, Hoffman T J et al. In vivo evaluation of an 111In-labeled ST-peptide analog for specific-targeting of human colon cancers. Nucl Med Biol 2001; 28:903-909.

What is claimed is:

1. A method of detecting neoplasia in a tissue sample from a patient having a phospholipase D (PLD) comprising the step of:
   quantifying the PLD protein activity level or the PLD mRNA level in the tissue sample; and
   determining whether the tissue sample has a lower level of protein activity than control or surrounding tissue region(s) wherein a lower activity region indicates detection and location of the neoplasia, or
   determining whether the tissue sample has a lower level of mRNA than control or surrounding tissue region(s) wherein a lower mRNA level region indicates detection and location of the neoplasia.

2. The method of detecting neoplasia of claim 1, wherein the PLD mRNA level is quantified by quantitative PCR (QPCR).

3. The method of detecting neoplasia of claim 1, wherein the patient having the lowered PLD protein activity level or the PLD mRNA is further administered with a phospholipid ether (PLE) analog selected from:

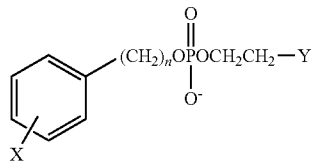

where X is selected from the group consisting of radioactive isotopes of halogen; n is an integer between 8 and 30; and Y is selected from the group comprising $NH_2$, $N(R)_2$ and $N(R)_3$, wherein R is an alkyl or arylalkyl substituent or

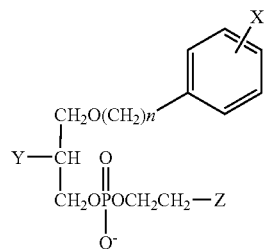

where X is a radioactive isotope of halogen; n is an integer between 8 and 30; Y is selected from the group consisting of H, OH, COOH, COOR and OR, and Z is selected from the group consisting of $NH_2$, $N(R)_2$ and $N(R)_3$, wherein R is an alkyl or arylalkyl substituent, whereby the administration of the PLE analog in the patient results in the treatment or reduction of said neoplasia in the patient.

4. The method of claim 3, wherein X is selected from the group of radioactive halogen isotopes consisting of $^{76}Br$, $^{77}Br$, $^{123}I$, $^{124}I$, $^{125}I$, $^{131}I$ and $^{211}At$.

5. The method of claim 3, wherein the phospholipid ether is 18-(p-Iodophenyl)octadecyl phosphocholine, 1-O-[18-(p-Iodophenyl)octadecyl]-1,3-propanediol-3-phosphocholine, or 1-O-[18-(p-Iodophenyl)octadecyl]-2-O-methyl-rac-glycero-3-phosphocholine, wherein iodine is in the form of a radioactive isotope.

6. The method of claim 3, wherein the PLE analog administered to the patient is further detected by PET, CT, MRI scanning methods and combination thereof.

7. The method of claim 1, wherein the tissue having the PLD is isolated with laser capture microdissection prior to quantifying the PLD protein level activity or the PLD mRNA activity.

8. The method of claim 1, wherein average ratio of PLD mRNA level in the control or the normal surrounding tissue to the neoplastic tissue is about 1.1 to about 3000.

9. The method of claim 1, wherein the neoplasia is selected from the group consisting of Lung cancer, Adrenal cancer, Melanoma, Colon cancer, Colorectal cancer, Ovarian cancer, Prostate cancer, Liver cancer, Subcutaneous cancer, Squamous cell cancer, Intestinal cancer, Hepatocellular carcinoma, Retinoblastoma, Cervical cancer, Glioma, Breast cancer, Pancreatic cancer and Carcinosarcoma.

* * * * *

UNITED STATES PATENT AND TRADEMARK OFFICE
CERTIFICATE OF CORRECTION

PATENT NO. : 7,632,644 B2  Page 1 of 1
APPLICATION NO. : 11/382645
DATED : December 15, 2009
INVENTOR(S) : Weichert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 705 days.

Signed and Sealed this

Second Day of November, 2010

David J. Kappos
*Director of the United States Patent and Trademark Office*

SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: PCR Primers

<400> SEQUENCE: 1
attcgttgga ggttggactg                                                 20

<210> SEQ ID NO 2
<211> LENGTH: 20
<212> TYPE: DNA
<213> ORGANISM: Artificial
<220> FEATURE:
<223> OTHER INFORMATION: PCR Primer

<400> SEQUENCE: 2
gtgctgtcaa tgctgctgat                                                 20

<210> SEQ ID NO 3
<211> LENGTH: 20
<212> TYPE: DNA
<213> ORGANISM: Artificial
<220> FEATURE:
<223> OTHER INFORMATION: PCR Primer

<400> SEQUENCE: 3
cagcagggac tctggagaac                                                 20

<210> SEQ ID NO 4
<211> LENGTH: 20
<212> TYPE: DNA
<213> ORGANISM: Artificial
<220> FEATURE:
<223> OTHER INFORMATION: PCR Primer -continued

```
<400> SEQUENCE: 4
ggatggttcc gtctctgtgt                                              20
```